April 20, 1965 O. O. DUNHAM Plant Pat. 2,494
CHRYSANTHEMUM PLANT
Filed Feb. 24, 1964
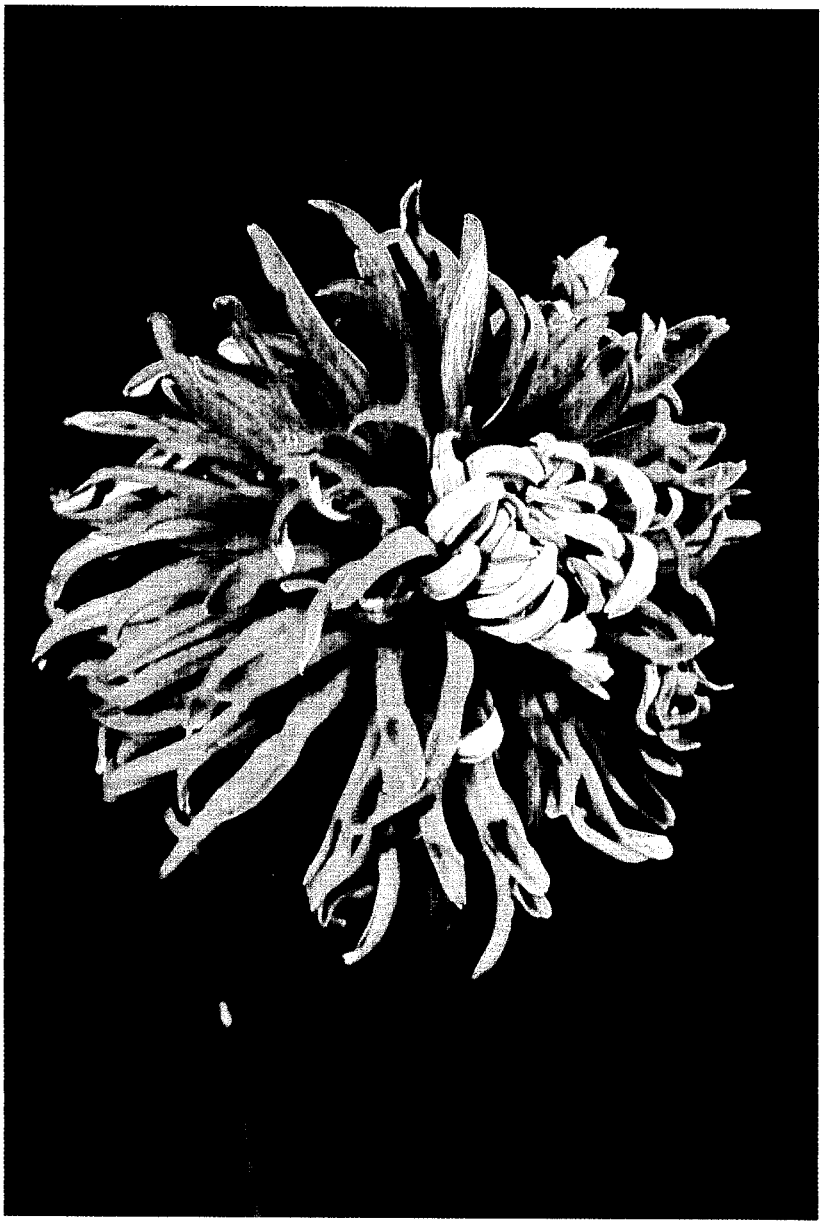
Inventor
O. O. Dunham
by Robb & Robb
attorneys United States Patent Office Plant Pat. 2,494
Patented Apr. 20, 1965

2,494
CHRYSANTHEMUM PLANT

Orville O. Dunham, Niles, Mich., assignor to Stern's Nurseries, Inc., Geneva, N.Y., a corporation of New York Filed Feb. 24, 1964, Ser. No. 347,079
1 Claim. (Cl. Plt.—82)

My present invention comprises a new and distinct variety of chrysanthemum plant, which is the result of crossing the variety "His Lordship," an unpatented variety of my own origination, with another variety of my own introduction which I designate "Ablaze" and which is likewise unpatented.

The object of this invention has been to produce a new variety of *Chrysanthemum indicum* which derives certain characteristics from each of the parents, in this particular instance the seed parent "His Lordship" contributing the multi-color effect, since "His Lordship" develops a bloom which has much darker reverses as well as a darker general overall appearance. The outer petals of my new variety are more reflexing and the center less incurving than the seed parent "His Lordship."

The much more reflexing form of blooms of the pollen parent is indicated in the blooms of my new variety by the form thereof, and thus the new variety is a combination of certain characteristics desired to be emphasized in contrast to the other varieties.

During the course of my hybridization of many different chrysanthemums, I have conducted an intensive program of development to provide new and distinct varieties, the instant variety being a product thereof which results from careful selection and cross-breeding of various chrysanthemum plants which in turn have been developed and introduced by me, constantly improving the characteristics and emphasizing those which are thought to be desirable.

The result of the hybridization previously referred to has been to produce my present new and distinct variety of chrysanthemum characterized by the dark reddish orange petals with pale orange-yellow reverses of incurving blooms which provide blooms with pale orange-yellow centers, the blooms being produced on vigorous, upright stems and being of large size, abundant foliage being further evident and the blooms appearing early and continuously until a killing frost.

More specifically the blooms of my new variety are of dark reddish-orange outer (Nickerson Color Fan published by The Munsell Color Company), with pale orange-yellow reverses, and with the center tightly balled. A multi-color appearance is provided especially when the tips of certain petals on the outer portion of the blooms present the reverse or portion thereof.

As grown in the vicinity of Niles, Michigan, in uniform culture, plants of my new variety grow to an average height of 18 to 20 inches with many blooms 6 inches in diameter thereon.

Under the conditions of culture previously mentioned which have been effected in the region of Niles, Michigan, plants of my new variety grow vigorously with profuse foliage in compact form.

My new variety when grown in the region of Niles, Michigan, blooms from mid-September and continues throughout the fall.

My new variety has been asexually reproduced by cuttings in the vicinity of Niles, Michigan, with observations made herein as a basis during October.

My new variety has been found to retain its distinctive characteristics throughout successive asexual reproduction.

The accompanying drawing forming a part hereof shows a typical plant of my new variety of chrysanthemum and a color illustration which is as reasonably accurate as is possible to provide in such color illustrations.

The following is a detailed description of my new variety of chrysanthemum plant, the color references being to the Nickerson Color Fan published by The Munsell Color Company:

*Description*

Parentage: Seedling.
- *Seed parent.*—"His Lordship" (unpatented).
- *Pollen parent.*—"Ablaze" (unpatented).

Classification: Botanic—*Chrysanthemum indicum.*

*Flower*

Blooming habit: Blooms profusely and continuously from mid-September until a killing frost.

Bud:
- *Size.*—Large.
- *Form.*—Short with flat top. Not substantially affected by hot or wet weather.

Color:
- *When sepals first divide.*—2.5R 4/10 Moderate Red.
- *When petals begin to unfurl.*—5R 3/7 Dark Red.
- *When half blown.*—Inside of petals—5R 4/12 Strong Red. Reverse of petals—7.5YR 9/4 Pale Orange-Yellow.
- *Sepals.*—Of no consequence.
- *Calyx.*—Shape—funnel. Size—Large and broad. Aspect—hairy.
- *Peduncle.* — Length — medium. Aspect — rough. Strength—stiff and erect. Bud opens well.

Bloom:
- *Size.*—Very large.
- *Average size when fully expanded.*—5½ to 6 inches.
- *Borne.*—In clusters and rounded.
- *Stems.*—Long and strong.
- *Form.*—When first open — cupped. Permanence — flattens.
- *Petalage.*—Very double; innumerable petals under normal conditions.

Color:
- *Center of flower.*—7.5R 4/11 Dark Reddish-Orange.
- *Outer petals.*—7.5R 4/11 Dark Reddish-Orange.
- *Base of petals.*—5R 3/7 Dark Red.
- *Inside of petals.*—5R 4/12 Strong Red.
- *Reverse of petals.*—7.5YR 9/4 Pale Orange-Yellow.
- *Discoloration.*—General tonality at end of: First week—moderate red with pale orange-yellow on reverse of petals. Second week—retains same color. Third week—retains same color.

Petals:
- *Texture.*—Thick and soft. Not affected by wet or hot weather.
- *Appearance.*—Inside—velvety. Outside—satiny.
- *Form.*—Pointed.
- *Arrangement.*—Irregular.
- *Persistence.*—Hang on and dry.
- *Fragrance.*—None.
- *Lastingness.*—On the plant—very long. As cut flower—very long.

Genital organs:
- *Stamens, anthers.*—Small, few.
- *Arrangement.*—Regular around styles.
- *Stamens, filaments.*—Medium.
- *Styles.*—Columnar.
- *Ovaries.*—All enclosed in calyx.

Plant:
- *Form.*—Bush.
- *Growth.*—Vigorous, upright and branching.

Foliage:
- *Size.*—Large.

*Quantity.*—Abundant.
*Shape.*—Lanceolate.
*Texture.*—Upper side — velvety. Under side — smooth. Ribs and veins—ordinary.
*Edge.*—Serrated.
*Serration.*—Very large.

I claim:

A new and distinct variety of chrysanthemum plant substantially as herein disclosed characterized as to novelty by the dark reddish-orange petals with pale orange-yellow reverses of incurving blooms which provide blooms with pale orange-yellow centers, the vigorous, upright form of growth, abundant foliage, the very large size of the blooms on long, strong stems, and its early, continuous period of bloom.

No references cited.

ABRAHAM G. STONE, *Primary Examiner.*